US009855109B2

(12) United States Patent
Dekel (10) Patent No.: US 9,855,109 B2
(45) Date of Patent: Jan. 2, 2018

(54) MEDICAL CART (71) Applicant: Claronav Inc., North York (CA)

(72) Inventor: Doron Dekel, Toronto (CA)

(73) Assignee: CLARONAV INC., Toronto (CA)

( * ) Notice: Subject to any disclaimer, the term of this patent is extended or adjusted under 35 U.S.C. 154(b) by 0 days.

(21) Appl. No.: 15/214,844

(22) PCT Filed: Feb. 17, 2015

(86) PCT No.: PCT/CA2015/050111
§ 371 (c)(1),
(2) Date: Jul. 20, 2016

(87) PCT Pub. No.: WO2015/120557
PCT Pub. Date: Aug. 20, 2015

(65) Prior Publication Data
US 2016/0367329 A1 Dec. 22, 2016

Related U.S. Application Data (60) Provisional application No. 61/940,750, filed on Feb. 17, 2014.

(51) Int. Cl.
*B62B 3/02* (2006.01)
*A61B 50/13* (2016.01)
(Continued)

(52) U.S. Cl.
CPC ............. *A61B 50/13* (2016.02); *A61B 50/10* (2016.02); *A61B 50/15* (2016.02); *A61B 50/20* (2016.02);
(Continued)

(58) Field of Classification Search
CPC ... B62B 3/02; F16M 11/2007; F16M 11/2021
(Continued)

(56) References Cited

U.S. PATENT DOCUMENTS 4,479,632 A * 10/1984 McIntire .................. B62B 3/04
254/10 B
4,934,659 A * 6/1990 Yoke ........................ B66D 5/14
254/326
(Continued)

FOREIGN PATENT DOCUMENTS

CA 2769509 2/2011
CN 2120566 11/1992
(Continued)

OTHER PUBLICATIONS

International Search Report and The Written Opinion for corresponding PCT Application No. PCT/CA2015/050111, dated Jun. 15, 2015.

*Primary Examiner* — Jeffrey J Restifo
(74) *Attorney, Agent, or Firm* — Bereskin & Parr LLP/S.E.N.C.R.L., s.r.l.

(57) ABSTRACT

A medical or dental cart for carrying medical or dental instruments. The cart comprises a base, a back pillar mounted on the base, a boom arm connected to the back pillar using hinged joints, and an instrument carrier connected to the boom arm using hinged joints. The instrument carrier is configured to carry medical or dental instruments. The hinged joints are configured such that the boom arm is rotatable toward the base and away from the base, and such that the instrument carrier is held at a substantially fixed orientation relative to the base throughout the range of motion of the boom arm. The hinged joints are also configured to impede sideways rotation, thereby impeding movement of the instrument carrier in a substantially sideways direction and thus impeding sideways tipping of the cart.

22 Claims, 4 Drawing Sheets

(51) Int. Cl.
*A61B 50/10* (2016.01)
*A61B 50/15* (2016.01)
*A61B 50/20* (2016.01)
*B62B 3/10* (2006.01)
*B62B 5/06* (2006.01)

(52) U.S. Cl.
CPC .................. *B62B 3/02* (2013.01); *B62B 3/10* (2013.01); *B62B 5/06* (2013.01)

(58) Field of Classification Search
USPC ............ 280/47.34, 47.35; 248/129, 130, 136
See application file for complete search history.

(56) References Cited

U.S. PATENT DOCUMENTS

| | | | | |
|---|---|---|---|---|
| 5,076,448 | A * | 12/1991 | Ballard | B66C 23/48 212/261 |
| 5,553,991 | A * | 9/1996 | Ferreira | B60B 29/002 280/47.34 |
| 8,172,242 | B1 * | 5/2012 | Crandall | A61B 5/0059 280/47.35 |
| 8,245,652 | B2 * | 8/2012 | Hung | A61G 12/001 108/147 |
| 8,474,835 | B1 * | 7/2013 | Rossi | B62B 3/02 280/47.35 |
| 8,567,798 | B2 * | 10/2013 | Rossini | A61G 12/001 280/43 |
| 8,677,911 | B2 * | 3/2014 | McRorie | G06F 1/1628 108/50.02 |
| 8,708,352 | B2 * | 4/2014 | Quirico | A61M 5/007 280/47.35 |
| 8,844,951 | B2 * | 9/2014 | De Jong | B62B 3/10 280/47.34 |
| 2001/0035702 | A1 * | 11/2001 | Murphy | A61G 12/001 312/229 |
| 2004/0262867 | A1 * | 12/2004 | Arceta | A61G 12/001 280/47.35 |
| 2005/0017468 | A1 * | 1/2005 | Gallant | A61G 7/05 280/47.35 |
| 2005/0275178 | A1 * | 12/2005 | Huesdash | A47B 57/482 280/47.35 |
| 2006/0050239 | A1 * | 3/2006 | Hashimoto | A61B 90/50 352/243 |
| 2006/0074406 | A1 * | 4/2006 | Cooper | A61B 19/2203 606/1 |
| 2007/0001413 | A1 * | 1/2007 | Rossini | A47B 21/00 280/47.35 |
| 2007/0228680 | A1 * | 10/2007 | Reppert | A47B 21/00 280/47.35 |
| 2008/0067302 | A1 * | 3/2008 | Olivera | F16M 11/08 248/183.1 |
| 2008/0234577 | A1 * | 9/2008 | Murkowski | A61B 8/00 600/437 |
| 2008/0252045 | A1 * | 10/2008 | Rossini | B62B 3/02 280/659 |
| 2009/0212518 | A1 * | 8/2009 | Bustle | A47B 21/0314 280/47.35 |
| 2009/0315287 | A1 * | 12/2009 | Rossini | A61G 12/001 280/47.35 |
| 2010/0148458 | A1 * | 6/2010 | Ross | A61M 16/0051 280/47.34 |
| 2010/0213679 | A1 * | 8/2010 | Smith | A47B 21/00 280/47.35 |
| 2011/0025007 | A1 * | 2/2011 | Butler | A61G 12/001 280/47.35 |
| 2011/0042911 | A1 * | 2/2011 | Kozlowski, Jr. | A47B 21/02 280/47.35 |
| 2011/0249805 | A1 * | 10/2011 | Kralles | A61B 6/4405 378/198 |
| 2012/0006767 | A1 * | 1/2012 | Bennett | A47B 81/00 211/26 |
| 2012/0126503 | A1 * | 5/2012 | Butler | A61G 12/001 280/47.35 |
| 2012/0212116 | A1 * | 8/2012 | McRorie | B62B 3/02 312/249.13 |
| 2013/0200579 | A1 * | 8/2013 | Abernethy | B62B 3/02 280/6.15 |
| 2013/0307236 | A1 * | 11/2013 | Lu | F16M 13/02 280/35 |
| 2013/0307237 | A1 * | 11/2013 | Chen | A61G 12/001 280/35 |
| 2014/0084558 | A1 * | 3/2014 | Ergun | B62B 3/005 280/47.35 |
| 2014/0218282 | A1 * | 8/2014 | Hung | G06F 3/01 345/156 |
| 2014/0265193 | A1 * | 9/2014 | Stark | B62B 3/10 280/47.34 |
| 2015/0021878 | A1 * | 1/2015 | Burke | A61B 19/0248 280/491.5 |
| 2015/0105660 | A1 * | 4/2015 | Ninomiya | B62B 3/02 600/437 |
| 2015/0166090 | A1 * | 6/2015 | Hardy | B62B 3/02 280/47.35 |
| 2015/0246681 | A1 * | 9/2015 | Raper, Jr. | B66F 5/02 254/4 R |
| 2015/0342562 | A1 * | 12/2015 | Messina | A61B 8/4405 248/544 |
| 2016/0157951 | A1 * | 6/2016 | Schoenig | A61G 7/0503 280/830 |
| 2016/0367329 | A1 * | 12/2016 | Dekel | A61B 50/10 |
| 2017/0027652 | A1 * | 2/2017 | Johnson | A61B 90/50 |
| 2017/0065355 | A1 * | 3/2017 | Ross | A61B 34/30 |

FOREIGN PATENT DOCUMENTS

| | | |
|---|---|---|
| KR | 100766333 | 10/2007 |
| WO | 2008053485 | 5/2008 |

* cited by examiner

MEDICAL CART

RELATED APPLICATIONS

This application is a National Stage of PCT Patent Application No. PCT/CA2015/050111 filed on Feb. 17, 2015, entitled "MEDICAL CART" which claims priority from the U.S. Provisional Patent Application No. 61/940,750, filed on Feb. 17, 2014, entitled "MEDICAL CART". The entirety of the contents of the PCT Patent Application No. PCT/CA2015/050111 and the U.S. Provisional Patent Application No. 61/940,750 are incorporated herein by reference.

FIELD

The present invention relates to the field of medicine, and more specifically to mobile mounting of devices used in performing medical procedures.

BACKGROUND

Medical professionals often need to position instruments, such as cameras, position trackers, patient monitors, display screens, laptop computers, etc. within a relatively short distance from the patient treatment region (eg, surgical field) at a height similar or higher than that of the patient.

SUMMARY

Embodiments of the current invention provide a mobile cart on which instruments such as cameras, position trackers, patient monitors, display screens, laptop computers, etc. may be mounted, with the following features:
1. Allows easily and rapidly changing the location and height of the mounted instruments by a clinician, including placing it over the patient.
2. Requires very small floor space at some distance from the treatment field, so minimizes interference with access to that field.
3. Allows positioning multiple devices together, stacked up vertically.
4. May be easily, rapidly and safely moved to/from storage and between treatment rooms.
5. Requires a small storage space.
6. Weighs only about 20-25 kg in total when designed to carry up to 5 kg of instruments.

In accordance with an aspect of an embodiment of the invention there is provided a medical or dental cart. The cart may comprise a base defining a base plane, and the base may be substantially horizontal. The base may have a plurality of supports for supporting the base for motion along a surface parallel to the base plane. The plurality of supports may include at least two rear supports and at least one front support. The at least two rear supports may define a rear support axis extending between the at least two rear supports parallel to the base plane. The at least one front support may be displaced in a frontward direction, parallel to the base plane, from the rear support axis. The at least one front support may be configured to support the base in a front support direction. The cart may further comprise a back pillar mounted vertically on the base. The back pillar may define a back pillar axis that is substantially orthogonal to the base plane. The back pillar may be mounted to the base such that the back pillar axis intersects the base plane closer to the rear support axis than to the front support direction. The cart may further comprise an instrument carrier, which may be configured to carry medical or dental instruments.

The cart may further comprise boom arm, which may be connected to the back pillar and the instrument carrier using hinged joints. The cart may further comprise a link arm, which may be connected to the back pillar and the instrument carrier using hinged joints. Hinged joints of the boom arm and the link arm may be configured to hold the instrument carrier at a substantially fixed orientation relative to the base plane throughout the range of motion of the boom arm and the link arm. The hinged joints on the back pillar may be positioned and oriented such that the boom arm may be rotatable towards the base to hold the instrument carrier substantially adjacent to the back pillar and the base plane during transport, and such that the boom arm may be rotatable away from the base to elevate and move the instrument carrier in the frontward direction relative to the back pillar axis and the at least one front support. The hinged joints may be configured to impede sideways rotation, thereby impeding movement of the instrument carrier in a substantially sideways direction to impede sideways tipping of the cart.

In accordance with a further aspect of an embodiment of the invention, the at least one front support may be configured to provide rotation of the base about the back pillar axis.

In accordance with a further aspect of an embodiment of the invention, each support in the at least one front support may be an omni-directional support, which may be configured to move the base in any direction parallel to the base plane.

In accordance with a further aspect of an embodiment of the invention, the instrument carrier may be substantially irrotational about the back pillar axis relative to the base plane.

In accordance with a further aspect of an embodiment of the invention, the hinged joints on the back pillar may be adjustable to stably support the instrument carrier in a plurality of different positions. When in different positions in the plurality of different positions, the instrument carrier may be at different heights from the base.

In accordance with a further aspect of an embodiment of the invention, the instrument carrier may comprise a support platform for providing a support surface. The instrument carrier may further comprise a pivotal coupling for attaching the support platform to a distal end of the boom arm. The distal end of the boom arm may be spaced from the back pillar. The pivotal coupling may be configured such that the support platform is pivotable relative to the back pillar axis. The pivotal coupling may also be configured to hold the support platform at a substantially fixed orientation relative to the base plane throughout the range of motion of the boom arm and the link arm.

In accordance with a further aspect of an embodiment of the invention, the base may be configured, and oriented relative to the back pillar, the boom arm, and the instrument carrier, to support without tipping a forward tipping moment. The forward tipping moment may result from a displacement of the boom arm and the instrument carrier in the frontward direction from the back pillar.

In accordance with a further aspect of an embodiment of the invention, the base may be configured, and oriented relative to the back pillar, the boom arm, and the instrument carrier, to support without tipping a forward tipping moment. The forward tipping moment may result from a displacement of the boom arm and the instrument carrier in the frontward direction from the back pillar, and a 5 kg weight supported by the instrument carrier.

In accordance with a further aspect of an embodiment of the invention, the base may be configured, and oriented such that a maximum forward tipping moment bearable by the base without tipping may be determinable. The maximum forward tipping moment may be a product of a forward tipping force and a frontward displacement in the frontward direction. The forward tipping force may be borne by the back pillar, acting toward the base plane, and may be displaced by the frontward displacement from the back pillar axis. The base may be further configured, and oriented such that a maximum backward tipping moment bearable by the base without tipping may be determinable. The maximum backward tipping moment may be a product of a backward tipping force and a backward displacement in a backward direction opposite to the frontward direction. The backward tipping force may be borne by the back pillar, acting toward the base plane, and may be displaced by the backward displacement from the back pillar axis. The maximum backward tipping moment may be less than half the maximum forward tipping moment.

In accordance with a further aspect of an embodiment of the invention, the base may be configured, and oriented such that a maximum first sideways tipping moment bearable by the base without tipping may be determinable. The maximum first sideways tipping moment may be a product of a first sideways tipping force and a sideways displacement in a first sideways direction. The first sideways direction may be orthogonal to the frontward direction and the back pillar axis, and may be orientated away from the back pillar axis towards one of the at least two rear supports. The first sideways tipping force may be borne by the back pillar, acting toward the base plane, and may be displaced by the sideways displacement from the back pillar axis. The base may be further configured and oriented such that a maximum second sideways tipping moment bearable by the base without tipping may be determinable. The maximum second sideways tipping moment may be a product of a second sideways tipping force and a second sideways displacement in a second sideways direction. The second sideways direction may be opposite to the first sideways direction. The second sideways tipping force may be borne by the back pillar, acting toward the base plane, and may be displaced by the sideways displacement from the back pillar axis. The maximum first sideways tipping moment and the maximum second sideways tipping moment may each be less than half the maximum forward tipping moment.

In accordance with a further aspect of an embodiment of the invention, each support in the plurality of supports may be one of a wheel and a ball, which may provide rolling motion along the surface parallel to the base plane.

In accordance with a further aspect of an embodiment of the invention, the instrument carrier being held substantially adjacent to the back pillar and the base plane during transport may define a storage and transport position. In the storage and transport position, the base may be configured such that the back pillar is tippable about the rear support axis, such that the at least two rear supports may support an entire weight of the cart. Each support in the at least two rear supports may be a fixed, uni-directional support, which may be configured to move the base in a horizontal direction orthogonal to the rear support axis.

In accordance with a further aspect of an embodiment of the invention, the cart may further comprise a handle, which may be supported by the back pillar and spaced from the base for holding and transporting the cart in the storage and transport position when the back pillar is tipped about the rear support axis such that the at least two rear supports support the entire weight of the cart.

In accordance with a further aspect of an embodiment of the invention, the at least two rear supports may comprise a first side support closest to a first side of the base and a second side support closest to a second side of the base. The second side may be opposite the first side. The second side support may be displaced from the first side support by between 10 and 50 cm. The at least one front support may define a front support axis, which may intersect the at least one front support and may be substantially parallel to the rear support axis. The front support axis may be displaced from the rear support axis by between 10 and 50 cm.

In accordance with a further aspect of an embodiment of the invention, the boom arm, link arm, instrument carrier, and back pillar may each be made of a lightweight material. The base may be made of a heavier material. The heavier material may have a density of at least twice the lightweight material.

In accordance with a further aspect of an embodiment of the invention, a centre of mass of the cart may be displaced within a centre of mass range. The centre of mass may be movable within the range by movement of the instrument carrier and the boom arm.

In accordance with a further aspect of an embodiment of the invention, a total weight of the cart may be less than 25 kg. In each different position in the plurality of different positions, the instrument carrier may be configured and positioned to support a weight of up to 5 kg without tipping the cart in any direction.

In accordance with a further aspect of an embodiment of the invention, in each different position in the plurality of different positions, the instrument carrier may be substantially parallel to the back pillar axis.

In accordance with a further aspect of an embodiment of the invention, in the storage and transport position, the instrument carrier may be held substantially adjacent to the back pillar and the base plane by a spring.

In accordance with a further aspect of an embodiment of the invention, the back pillar may comprise a recess for receiving the boom arm when in the storage and transport position, such that the boom arm in the storage and transport position may be substantially parallel to and coincident with the back pillar axis.

In accordance with a further aspect of an embodiment of the invention, each support in the plurality of supports may define a diameter. The diameter of each support in the at least two rear supports may be at least 50% larger than the diameter of each support in the at least one front support.

DRAWINGS

The person skilled in the art will understand that the drawings, described below, are for illustration purposes only. The drawings are not intended to limit the scope of the applicants' teachings in any way.

DESCRIPTION OF PREFERRED EMBODIMENT

Figure 1:
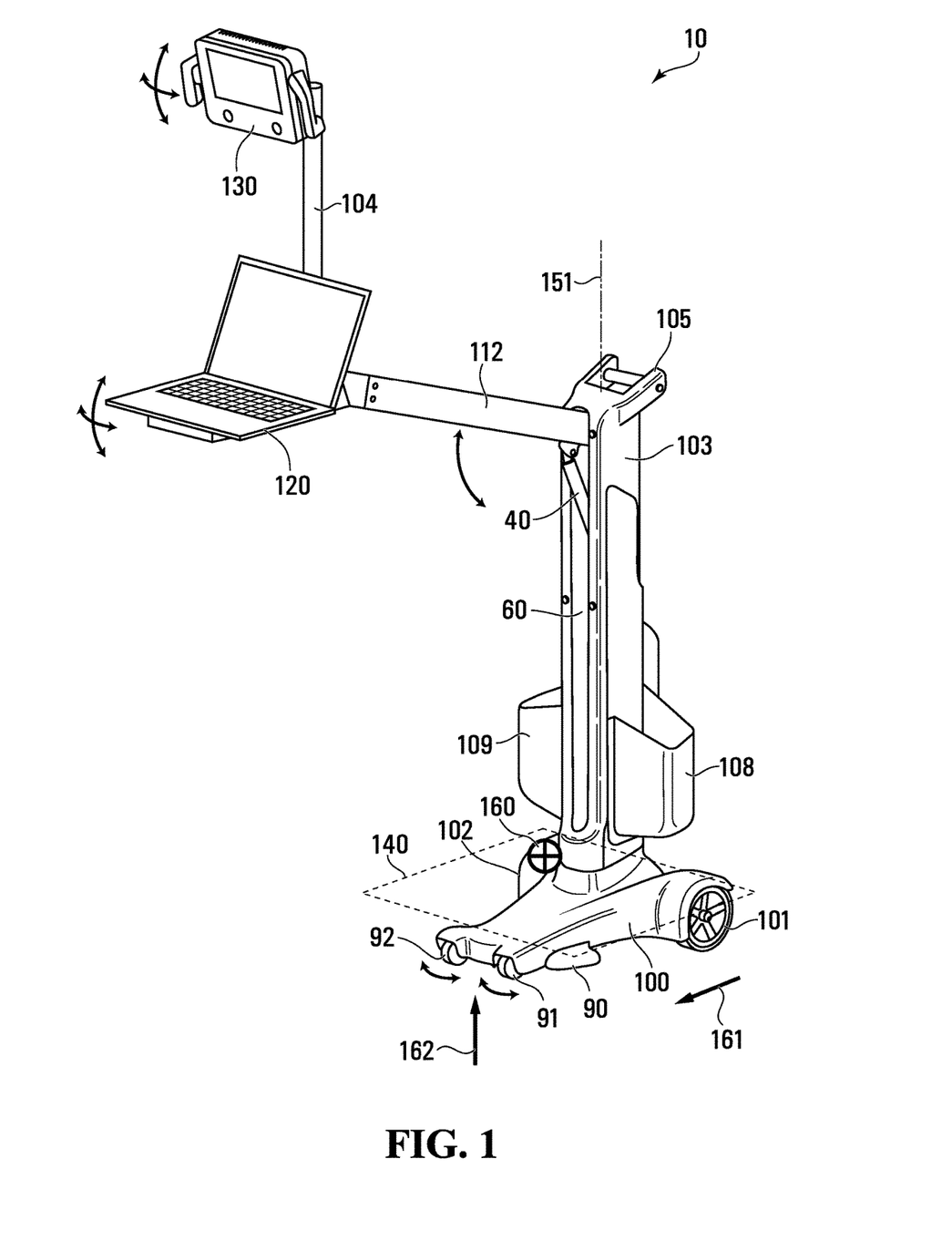
FIG. 1 illustrates a cart according to one embodiment of the present invention, with its boom arm in the operative position to carry instruments during a medical or dental procedure.
Figure 2:
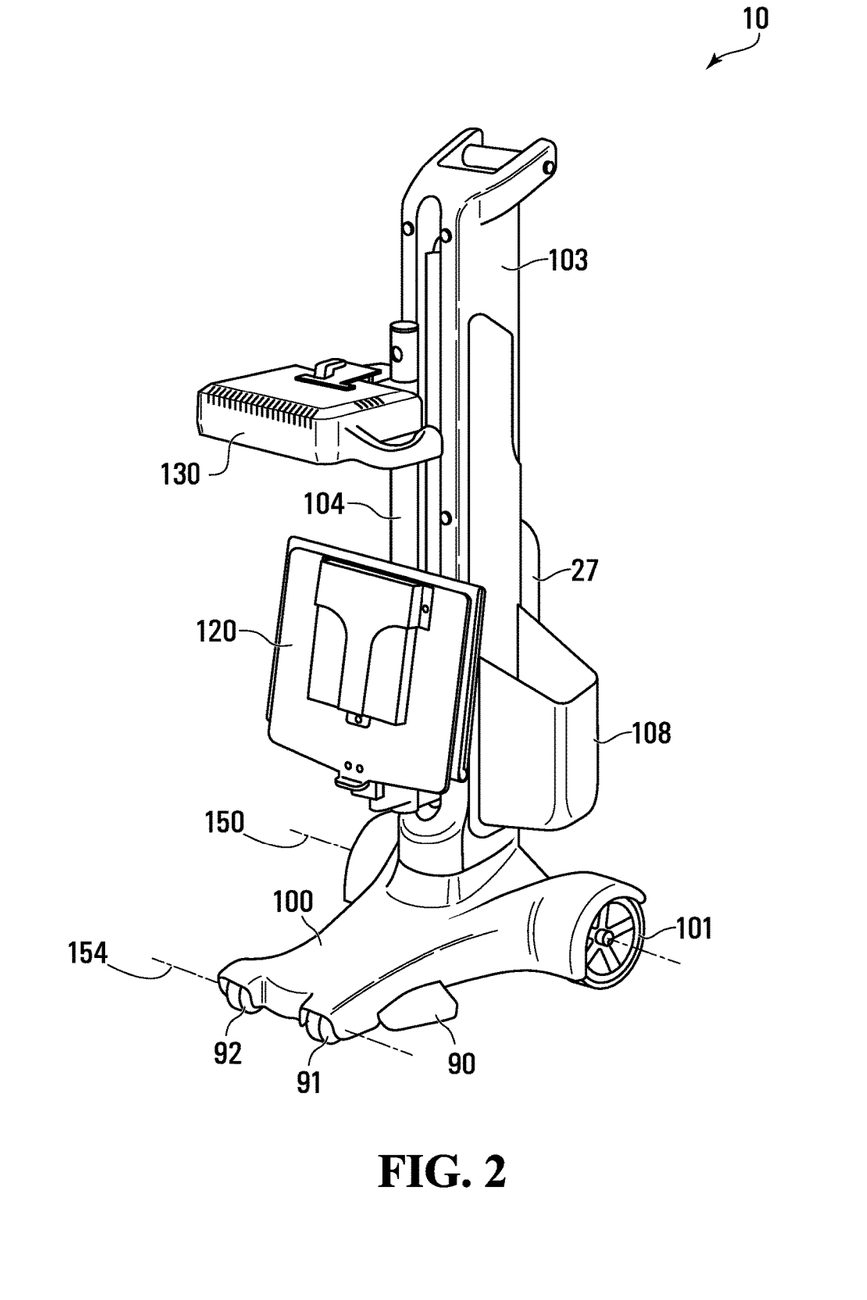
FIG. 2 illustrates a cart with its boom arm folded down in the storage and transport position according to one embodiment of the present invention.
Figure 3A:
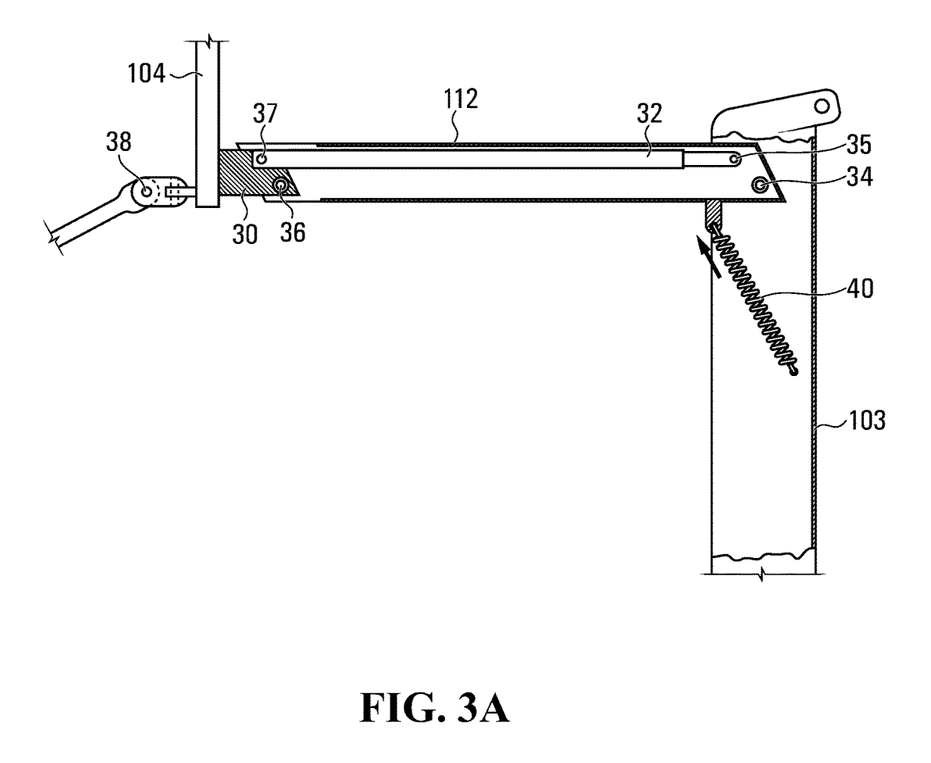
FIG. 3A, in a cross-sectional view, illustrates a portion of the cart, including the adjustable instruments support structure, with the boom arm extended as shown in FIG. 1.
Figure 3B:
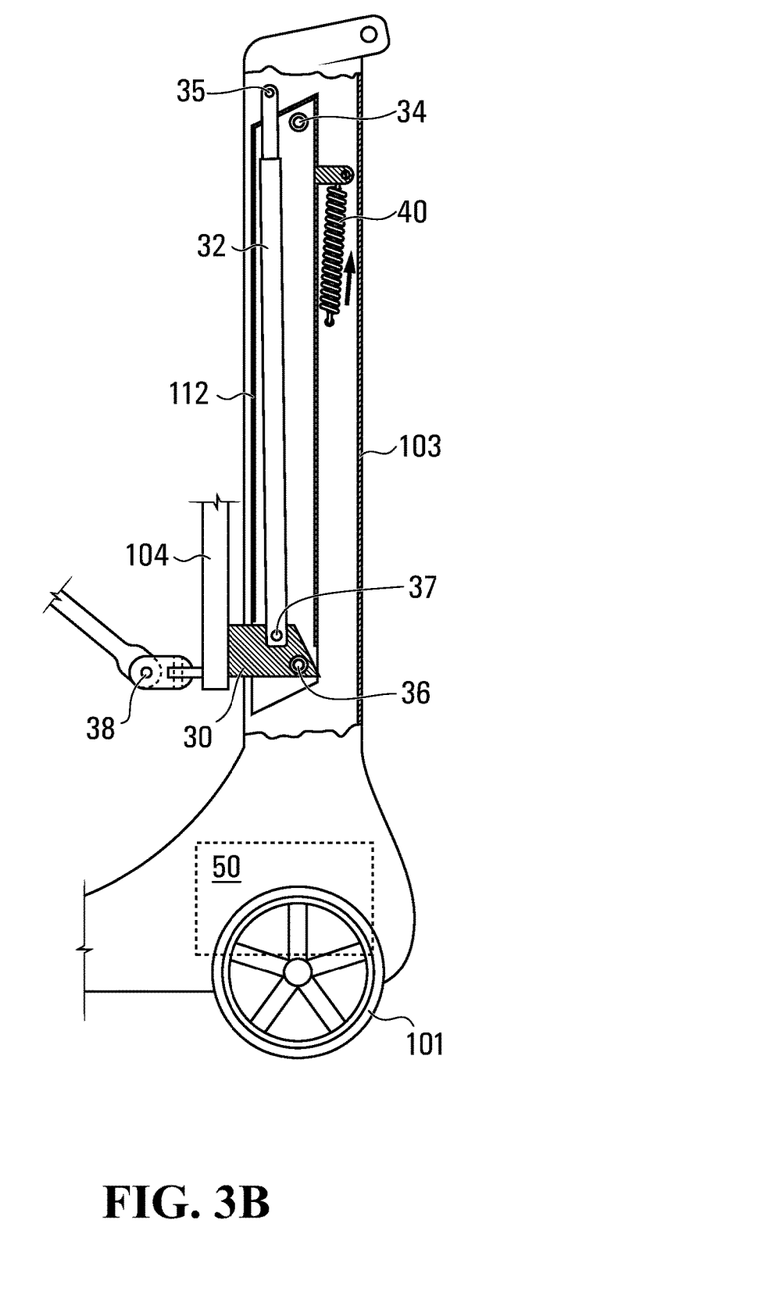
FIG. 3B, in a cross-sectional view, illustrates a portion of the cart, including the adjustable instruments support structure and the base, with its boom arm in a storage and transport position as shown in FIG. 2.

Referring to FIGS. 1-3, the main structural parts of the cart 10 are mobile base 100, back pillar 103 mounted vertically on top of the base 100 and orthogonal to the base plane 140, a hollow boom arm 112 connected to the back pillar 103 through hinged joint 34, and an instrument carrier 104 connected to boom arm 112 through hinged joint 36 and held substantially parallel to the back pillar axis 151 using link arm 32. Four wheels may be fixed to the base 100, with the two front wheels 91, 92 being omni-directional wheels (or balls), able to move in any direction, including sideways. The wheels (or balls) may be configured to allow the cart 10 to roll along the ground, either to and from storage, or into position at a desired distance from the treatment field. The two front wheels 91, 92 may be displaced in the frontward direction 161 relative to the back wheels 101, 102. The instruments to be carried by the cart 10 may be attached to instrument carrier 104, either through rigid clamps or through pivotal couplings 38, allowing each instrument to be rotated and/or tilted individually.

The instruments may also be supported by a support platform, which may be connected to the boom arm 112 and instrument carrier 104 via pivotal coupling 38. In a preferred embodiment, the pivotal coupling 38 may be configured such that the support platform is pivotable about an axis parallel to the back pillar axis 151. The attitude (azimuth and elevation) of each device or support platform attached to instrument carrier 104 can be adjusted using a pivotal coupling 38, which can be a friction/lockable ball joint or, preferably, two separate rotational joints. The pivotal coupling 38 may thus be configured to hold the instruments or support platform in a fixed position, subject to manual rotation and or/tilting, such that the instruments or support platform can maintain a substantially fixed orientation relative to the base plane 140 throughout the range of motion of the boom arm 112 and the link arm 32.

Link arm 32 can keep the instruments at a constant attitude throughout the range of motion of the boom arm 112, and can be hidden inside hollow boom arm 112. Power and signal cables may be hidden inside back pillar 103, boom arm 112 and instrument carrier 104, protecting them from damage and reducing visual clutter. A power cable may exit the base 100 at the back, between back wheels 101, 102. Excess cable can be wrapped around spindle 27 (or two opposing hooks) at the back of back pillar 103. Compression spring 40 provides support for the boom arm 112 to counter gravitation when it is open, and a positive locking force when the boom arm 112 is closed. Ballast 50 may be mounted above the back wheels 101, 102 to provide stability to, and impede tipping of, the cart 10.

Foot rests 90 on the sides of the base 100 allow users to hold the base 100 stable on the floor while pulling or pushing the instrument carrier 104 during movement of the boom arm 112 into and out of the storage and transport position, and throughout the range of motion in the operative position. Baskets 108, 109 on the sides of the cart 10 provide storage space for small accessories and literature. Handrail 105 can allow a user to easily move the cart 10, when in the storage and transport position, by tilting the back pillar 103 about the rear support axis 150 and rolling it on its back wheels 101, 102 (similar to a dolly/hand-truck). In a preferred embodiment, when in the storage and transport position, back wheels 101, 102 may support an entire weight of the cart, and may be configured to provide movement of the base 100 along the ground in a direction that is orthogonal to the rear support axis 150. While the back wheels 101, 102 may support an entire weight of the cart 10 and can provide smooth travel over uneven surface during long transport, the front wheels 91, 92 are lifted off the ground during the transport. The back wheels may, therefore, have a diameter larger by 50% or more than the front wheels.

In one embodiment, a laptop computer 120 and an enclosure 130 containing a stereoscopic camera and an illumination panel are attached to the instrument carrier 104.

FIGS. 1 and 3A show the cart 10 in the operative position, where the base 100 may be positioned next to the patient's bed or chair, and the instruments may be placed above and next to the treatment field anywhere in the patient's body. The combination of the upward force applied by compression spring 40 and the friction in hinged joint 34 can hold the instruments in a desired position. FIG. 2 shows the cart 10 in the storage and transport position, ready to be moved or stored. To open the cart 10, the user may place one foot on footrest 90 and pull instrument carrier 104 forward and up.

The force applied by spring 40 may be adjusted to balance the weight of the instruments being carried (payload) when the boom arm 112 is in different positions. Preferably, spring 40 is a gas spring and the internal pressure may be adjusted to control the force. Alternatively, or in addition, the force may also be adjusted by moving one end of the spring 40 closer to, or farther from, the other end of the spring 40 using a screw. To allow stable positioning over a wide range of boom arm elevation angles, for example, from 30 degrees below horizontal to 45 above horizontal, friction may be added to hinged joint 34. The friction in hinged joint 34 may be adjusted, at the factory and later by users, to provide a balance between ease of movement on the one hand, and resistance to "drift" of the boom arm 112 from its intended position on the other. The friction in hinged joint 34 may be provided by a washer-like friction plate surrounding the axle of hinged joint 34, pressed against an opposing steel (or other friction-coated) surface by a spring force. The force of the friction spring can be adjusted by the user using an adjustment screw.

To adjust the height and position of instrument carrier 104, the user may grab and move the instrument carrier 104, or the instruments attached to it. Movement of instrument carrier 104 and the boom arm 112 in a substantially sideways direction may be impeded by hinged joints 34, 35. In some embodiments, the hinged joints 34, 35 may be located at least partly within a recess 60 of the back pillar 103, such that the portions of the back pillar 103 forming the sidewalls of the recess 60 themselves prevent substantial sideways motion of the boom arm 112. Movement of just the instrument carrier 104 in a substantially sideways direction relative to the boom arm 112 may be impeded by hinged joints 36, 37 to impede sideways rotation in order to impede sideways tipping of the cart 10. The front wheels 91, 92 allow the instrument carrier 104 to move in a substantially sideways direction, since the front wheels 91, 92 can rotate about the back pillar axis 151 when it is located approximately between back wheels 101, 102.

Hollow boom arm 112 may be connected through hinged joint 36 to block 30, which is rigidly attached to instrument carrier 104, on one side, and through hinged joint 34 to back pillar 103, on the other side. Link arm 32, hidden inside hollow boom arm 112, may be connected through hinged joint 35 to back pillar 103 on one side, and through hinged joint 37 to block 30 on the other side. Hinged joints 34, 35, 36, 37 may be arranged in a parallelogram, such that the link arm 32 may be kept substantially parallel to the boom arm 112, and such that the instrument carrier 104 may be held at a substantially fixed orientation relative to the base plane 140, throughout the range of movement of boom arm 112. Thus, at any given point in the range of movement of boom arm 112, instrument carrier 104 may be at a different height from the base 100. Hinged joints 34, 35 may be configured to limit the range of movement of the boom arm 112, and thus the range of movement of the instrument carrier 104, to positions in the frontward direction relative to the back pillar axis 151. Instrument carrier 104 may thus remain substantially parallel to back pillar axis 151 throughout the range of motion of boom arm 112, keeping the attitude of the instruments constant as the user moves instrument carrier 104 about. In the parallelogram configuration, hinged joint 35 may be offset from hinged joint 34, and hinged joint 37 may be offset from hinged joint 36, to allow the boom arm 112 a range of motion from about 90 degrees below horizontal to about 45 degrees above horizontal.

When the boom arm 112 is moving within its range of movement, hinged joints 34, 35 may impede the movement of boom arm 112 in a substantially sideways direction. Hinged joints 34, 35 may be configured to impede sideways rotation in order to impede sideways tipping of the cart 10. The front wheels 91, 92 may allow the boom arm 112 to move in a substantially sideways direction, since the front wheels 91, 92 can rotate about the back pillar axis 151.

In one embodiment, the distance between the two back wheels 101, 102, and the distance between the front support axis 154 and the rear support axis 150, may each be about 10-50 cm. A plate may hold the back wheels 101, 102 and back pillar 103 in place. The height of hinged joint 34 from the floor may be about 90 cm, and the boom arm 112 may be about 70 cm long, allowing the bottom of instrument carrier 104 to operate at a height range of about 60-135 cm, which is sufficient for accommodating a wide range of patient treatment setups and user preferences. In this embodiment, the range of motion of the boom arm 112 may allow the range of positions of the instrument carrier 104 to include positions displaced in the frontward direction 161 relative to the front wheels 91, 92.

Ballast 50 may be placed above, or around, the rear support axis 150, to counter-balance the weight of the boom arm 112, instrument carrier 104, and the instruments that the instrument carrier 104 carries when the cart 10 is in the operative position. The support provided by the front wheels 91, 92 in the front support direction 162 may also help to counter-balance the weight of the boom arm 112, instrument carrier 104, and the instruments that the instrument carrier 104 carries when the cart 10 is in the operative position. The front support direction 162 may be orientated to impede frontward tipping of the base 100.

The displacement in the frontward direction 161 of the boom arm 112, the instrument carrier 104, and the instruments that the instrument carrier 104 carries when the cart 10 is in the operative position may create a forward tipping moment. The forward tipping moment may be borne by the back pillar 103 so as to impede tipping of the cart 10. It is contemplated that tipping moments may occur in directions other than the frontward direction 161, such as in a backward direction opposite to the frontward direction 161, or in a sideways direction. Since the boom arm 112 and the instrument carrier 104 may be configured such that their ranges of motion may be limited to positions in the frontward direction 161 relative to the back pillar axis 151, a backward or sideways tipping moment would typically be smaller than a forward tipping moment. In a particular embodiment, a maximum tipping moment in the backward direction opposite to the frontward direction 161, or in a sideways direction orthogonal to the frontward direction 161 and parallel to the base plane 140, may be less than half of the maximum forward tipping moment (all tipping moments being measured relative to the back pillar axis 151). In other embodiments, the maximum tipping moment in the backward direction opposite to the frontward direction 161, or in the sideways direction orthogonal to the frontward direction 161 and parallel to the base plane 140, may be less than 40%, 30%, 20% or even 10% of the maximum forward tipping moment.

The base 100 is configured to resist the forward tipping moment caused by the displacement of the boom arm 112 and the instrument carrier 104 in the frontward direction 161, whether or not there is instruments attached to the instrument carrier 104. In a preferred embodiment, the weight that may be supported by the instrument carrier 104 is about 5 kg.

In one embodiment, a total weight of the cart 10 may be less than 25 kg. In a preferred embodiment, when the boom arm 112 is moving within its range of movement in the frontward direction 161 relative to the rear support axis 150, the instrument carrier 104 may be configured and positioned to support a weight of up to 5 kg. Since movement of the instrument carrier 104 can be impeded in a substantially sideways direction, the weight of ballast 50 and base 100, as well as the support provided by the front wheels 91, 92 can be sufficient to impede tipping of the cart 10 in any direction.

The centre of mass 160 of the cart 10 may move. Since the cart 10 can include moving components, the centre of mass 160 may be displaced in the frontward direction 161 or in a backward direction opposite to the frontward direction 161 by movement of the boom arm 112 and instrument carrier 104.

Back wheels 101, 102 may be uni-directional wheels (or balls). Front wheels 91, 92 may be smaller omni-directional wheels FIGS. 2 and 3B show the cart 10 in the storage and transport position, which may be used for shipping, storage or moving between locations. In this state, boom arm 112 may be at a position that is at or near an endpoint of the range of motion allowed by the hinged joints 34, 35, such that boom arm 112 and instrument carrier 104 are positioned adjacent to back pillar 103, and substantially parallel to back pillar axis 151. Boom arm 112 may further be located in a recess 60 in the back pillar 103, such that the boom arm 112 is aligned with the back pillar axis 151. In this embodiment, there may be sufficient space between the back pillar 103 and the instrument carrier 104 for the user to grab the instrument carrier 104 as needed to move the cart 10 into the operative position. When the cart 10 is in the storage and transport position, spring 40 may apply a force on boom arm 113 in the opposite rotational direction than when the boom arm 113 is in the operative position, thereby applying an extra "locking" force on the boom arm 112 to prevent it from rising up unintentionally. In one embodiment, a unidirectional rotary damper may be added to one of the hinged joints 34, 35, 36, or 37. In another embodiment, a soft rubber bumper may be added to back pillar 103, facing the boom arm 112, to slow and soften the movement of the boom arm 112 into the storage and transport position.

To keep the center of mass 160 of the cart 10 as low as possible, parts located above the base 100, especially the boom arm 112 and anything connected to it, and including the back pillar 103, may be made of either a strong plastic (such as polycarbonate) or a thin metal alloy with a high tensile strength to weight ratio, such as aluminum 6061-T6 or Chromoly steel. Alternatively, the parts located above the base 100 may be made of carbon fibre, fiberglass, or titanium. The base 100 may be made of a heavier material, such as steel, or another high-density metal or metal alloy. In a preferred embodiment, the material of the base may have a density twice as large as that of the material of the boom arm, link arm, back pillar, and instrument carrier. The weight of the base 100 may help to impede frontward tipping of the cart 10. Ballast 50 is preferably made of a low cost material with a high specific weight, such as iron or copper. The base 100 and the sides of back pillar 103 may be covered in thin plastic sheets to make them more visually attractive.

A handrail 105 may be located at the top of back pillar 103 to allow users to easily grab and tilt the cart 10 back, and to then roll it behind them (or in front of them) as they walk. The narrow wheel base of the cart 10 can reduce the likelihood that a user's leg will hit the cart 10 unintentionally during walking. Baskets 108, 109 may be added to the sides of back pillar 103 for the storage of accessories, without substantially increasing the overall width of the cart 10 or substantially raising its center of mass 160.

It will be understood that other variations and modifications of the invention are possibly. All such modifications and variations are believed to be within the sphere and scope of the invention as defined by the claims appended hereto.

What is claimed is:

1. A medical or dental cart comprising
a base defining a base plane and having a plurality of supports for supporting the base for motion along a surface parallel to the base plane, the base being substantially horizontal when the plurality of supports are supported by the ground, the plurality of supports including at least two rear supports, and at least one front support, the at least two rear supports, defining a rear support axis extending between the at least two rear supports, parallel to the base plane, and the at least one front support, being displaced in a frontward direction, parallel to the base plane, from the rear support axis, the at least one front support, being configured to support the base in a front support direction;
a back pillar mounted vertically on the base and defining a back pillar axis substantially orthogonal to the base plane, the back pillar being mounted to the base such that the back pillar axis intersects the base plane closer to the rear support axis than to the front support direction;
an instrument carrier configured to carry medical or dental instruments;
a boom arm connected to the back pillar and the instrument carrier using hinged joints;
a link arm connected to the back pillar and the instrument carrier using hinged joints;
wherein the hinged joints of the boom arm and the link arm are configured to hold the instrument carrier at a substantially fixed orientation relative to the base plane throughout the range of motion of the boom arm and the link arm; and
wherein the hinged joints on the back pillar are positioned and oriented such that the boom arm is rotatable towards the base to hold the instrument carrier substantially adjacent to the back pillar and the base plane during transport, and is rotatable away from the base to elevate and move the instrument carrier in the frontward direction relative to the back pillar axis and the at least one front support; and
wherein the hinged joints are configured to impede sideways rotation, thereby impeding movement of the instrument carrier in a substantially sideways direction to impede sideways tipping of the cart.

2. The cart as defined in claim 1 wherein the at least one front support, is configured to provide rotation of the base about the back pillar axis.

3. The cart as defined in claim 1 wherein each support in the at least one front support, is an omni-directional support configured to move the base in any direction parallel to the base plane.

4. The cart as defined in claim 1 wherein the instrument carrier is substantially irrotational about the back pillar axis relative to the base plane.

5. The cart as defined in claim 1 wherein
the hinged joints, on the back pillar are adjustable to stably support the instrument carrier in a plurality of different positions; and
when in different positions in the plurality of different positions, the instrument carrier is at different heights from the base, and is displaced in the frontward direction from the back pillar axis.

6. The cart as defined in claim 5, wherein
a total weight of the cart is less than 25 kg,
in each different position in the plurality of different positions, the instrument carrier is configured and positioned to support a weight of up to 5 kg without tipping the cart in any direction.

7. The cart as defined in claim 5, wherein in each different position in the plurality of different positions, the instrument carrier is substantially parallel to the back pillar axis.

8. The cart as defined in claim 1 wherein the instrument carrier comprises a support platform for providing a support surface, and a pivotal coupling for attaching the support platform to a distal end of the boom arm, the distal end being spaced from the back pillar, wherein
the pivotal coupling is configured such that the support platform is pivotable about an axis parallel to the back pillar axis; and
the pivotal coupling is configured to hold the support platform at a substantially fixed orientation relative to the base plane throughout the range of motion of the boom arm and the link arm.

9. The cart as defined in claim 1 wherein the base is configured, and oriented relative to the back pillar, the boom arm, and the instrument carrier, to support without tipping a forward tipping moment resulting from a displacement of the boom arm and the instrument carrier in the frontward direction from the back pillar.

10. The cart as defined in claim 1 wherein the base is configured, and oriented relative to the back pillar, the boom arm, and the instrument carrier, to support without tipping a forward tipping moment resulting from a displacement of the boom arm and the instrument carrier in the frontward direction from the back pillar, and a weight of about 5 kg supported by the instrument carrier.

11. The cart as defined in claim 1 wherein the base is configured, and oriented such that
a maximum forward tipping moment bearable by the base without tipping is determinable, the maximum forward tipping moment being a product of a forward tipping force and a frontward displacement in the frontward direction, the forward tipping force being borne by the back pillar, acting toward the base plane, and displaced by the frontward displacement from the back pillar axis;

a maximum backward tipping moment bearable by the base without tipping is determinable, the maximum backward tipping moment being a product of a backward tipping force and a backward displacement in a backward direction opposite to the frontward direction, the backward tipping force being borne by the back pillar, acting toward the base plane, and displaced by the backward displacement from the back pillar axis;

the maximum backward tipping moment is less than half the maximum forward tipping moment.

12. The cart as defined in claim 1 wherein the base is configured and oriented such that a maximum first sideways tipping moment bearable by the base without tipping is determinable, the maximum first sideways tipping moment being a product of a first sideways tipping force and a sideways displacement in a first sideways direction, the first sideways direction being orthogonal to the frontward direction and the back pillar axis and orientated away from the back pillar axis towards one of the at least two rear supports, the first sideways tipping force being borne by the back pillar, acting toward the base plane, and displaced by the sideways displacement from the back pillar axis;

a maximum second sideways tipping moment bearable by the base without tipping is determinable, the maximum second sideways tipping moment being a product of a second sideways tipping force and a sideways displacement in a second sideways direction opposite to the first sideways direction, the second sideways tipping force being borne by the back pillar, acting toward the base plane, and displaced by the sideways displacement from the back pillar axis;

the maximum first sideways tipping moment and the maximum second sideways tipping moment are each less than half the maximum forward tipping moment.

13. The cart as defined in claim 1 wherein each support in the plurality of supports is one of a wheel and a ball to provide rolling motion along the surface parallel to the base plane.

14. The cart as defined in claim 1, wherein the instrument carrier being held substantially adjacent to the back pillar and the base plane during transport defines a storage and transport position, wherein in the storage and transport position, the base is configured such that the back pillar is tippable about the rear support axis such that the at least two rear supports, support an entire weight of the cart; and each support in the at least two rear supports, is a fixed, uni-directional support configured to move the base in a horizontal direction orthogonal to the rear support axis.

15. The cart as defined in claim 14 further comprising a handle supported by the back pillar and spaced from the base for holding and transporting the cart in the storage and transport position when the back pillar is tipped about the rear support axis such that the at least two rear supports, support the entire weight of the cart.

16. The cart as defined in claim 14, wherein in the storage and transport position, the instrument carrier is held substantially adjacent to the back pillar and the base plane by a spring.

17. The cart as defined in claim 14, wherein the back pillar comprises a recess for receiving the boom arm when in the storage and transport position, such that the boom arm in the storage and transport position is substantially parallel to and coincident with the back pillar axis.

18. The cart as defined in claim 1, wherein the at least two rear supports, comprise a first side support closest to a first side of the base and a second side support closest to a second side of the base, the second side being opposite the first side, the second side support being displaced from the first side support by between 10 and 50 cm; and the at least one front support, defines a front support axis intersecting the at least one front support, and being substantially parallel to the rear support axis, the front support axis being displaced from the rear support axis by between 10 and 50 cm.

19. The cart as defined in claim 1, wherein the boom arm, link arm and the instrument carrier, are each made of a lightweight material; and the base is made of a heavier material, the heavier material having a density of at least twice the lightweight material.

20. The cart as defined in claim 1, wherein a center of mass of the cart is displaced within a center of mass range in the frontward direction from the back pillar axis and in the backward direction from the at least one front support, the center of mass being movable within the range by movement of the instrument carrier and the boom arm.

21. The cart as defined in claim 1, wherein each support in the plurality of supports defines a diameter, the diameter of each support in the at least two rear supports, being at least 50% larger than the diameter of each support in the at least one front support.

22. The cart as defined in claim 1, wherein boom arm comprises a hollow core and link arm passes through the hollow core.

* * * * *